United States Patent [19]

Takagi et al.

[11] Patent Number: 5,322,946
[45] Date of Patent: Jun. 21, 1994

[54] PROCESS FOR PRODUCING AROMATIC HYDROXY COMPOUND

[75] Inventors: Masato Takagi; Yoshihiro Naruse; Akinori Matsuura; Kyohko Kobayashi, all of Chiba, Japan

[73] Assignee: Kawasaki Steel Corporation, Japan

[21] Appl. No.: 2,420

[22] Filed: Jan. 8, 1993

Related U.S. Application Data

[63] Continuation of Ser. No. 770,108, Oct. 2, 1991, abandoned.

[30] Foreign Application Priority Data

Oct. 4, 1990 [JP] Japan .................................. 2-266994
Jun. 13, 1991 [JP] Japan .................................. 3-141853

[51] Int. Cl.⁵ ..................... C07C 37/04; C07D 215/20
[52] U.S. Cl. ..................................... 546/179; 568/738; 568/769; 568/795; 552/261; 552/262; 546/290
[58] Field of Search ................ 568/769, 795, 738; 546/179, 290; 552/261, 262

[56] References Cited

U.S. PATENT DOCUMENTS 2,452,404 10/1948 Tyrer ................................. 568/738
4,633,024 12/1986 Ueno et al. ........................ 568/738

FOREIGN PATENT DOCUMENTS 2706316 8/1978 Fed. Rep. of Germany .

OTHER PUBLICATIONS

Schwartz et al., Surface Active Agents 1949, pp. 8, 516.

*Primary Examiner*—Howard T. Mars
*Assistant Examiner*—Rebecca Cook
*Attorney, Agent, or Firm*—Bierman and Muserlian

[57] ABSTRACT

An industrially useful process for the production of an aromatic hydroxy compound which comprises reacting an aromatic sulfonic acid alkali metal salt and/or an aromatic sulfonic acid with an alkali metal hydroxide in the presence of a surface active agent, wherein the reaction is effected by uniformly dispersing these-materials in a reaction medium selected from aliphatic, alicyclic and aromatic hydrocarbons. By employing this process, the product can be obtained with high purity, high yield and high selectivity using a minimum amount of the alkali metal hydroxide.

5 Claims, No Drawings

PROCESS FOR PRODUCING AROMATIC HYDROXY COMPOUND

This application is a continuation of U.S. patent application Ser. No. 770,108 filed Oct. 2, 1991, now abandoned.

FIELD OF THE INVENTION

This invention relates to a process for the production of aromatic hydroxy compounds, and more particularly to a process which can produce an aromatic hydroxy compound of interest with high purity, high yield and high selectivity using a minimum amount of an alkali metal hydroxide.

BACKGROUND OF THE INVENTION

An alkali fusion process has been applied for a long time to the production of aromatic hydroxy compounds from alkali salts of aromatic sulfonic acids by reacting the Starting material with an alkali metal hydroxide. This process, however, has a disadvantage in that agitation and mixing of the reaction materials become difficult as the reaction proceeds, as well as a foaming problem, because the reaction mixture changes its phase from liquid to powder via a slurry phase and a high viscosity phase with the progress of the reaction.

As countermeasures to overcome such problems, several processes have been proposed, for example, (1) a process in which a high power agitation apparatus or a mixing apparatus of a multiblade type is used (JP-B 33-9970), (2) a process in which an alkali material is added to the reaction mixture with the aim of keeping the reaction in powder phase throughout the entire reaction period (JP-A 51-52142), (3) a process in which an alkali material is used in an excess amount to fluidize the reaction mixture and (4) a process in which the reaction is effected under a pressured condition in the presence of water. (The terms "JP-B" and "JP-A" as used herein mean an "examined Japanese patent publication" and an "unexamined published Japanese patent application", respectively) These prior art processes, however, still have disadvantages. For instance, the above processes 1 and 4 require special equipments which entail expensive facility costs, the process 2 requires complex handling because not only it is difficult to keep the reaction mixture in powder form but also it is necessary to modify the agitation system and the process 3 cannot prevent foaming even by the use of an excess amount of the alkali-material in addition to a necessity to use a large quantity of acid to neutralize the alkali material remained in a large quantity after the reaction and Such a neutralization step generates a large volume of waste water which causes a problem of requiring additional treatment cost.

In consequence, for the purpose of improving fluidity of a reaction mixture in the alkali fusion reaction, further modified processes have been proposed in which reaction of an alkali salt of an aromatic sulfonic acid with an alkali metal hydroxide is carried out by uniformly dispersing in an inert solvent as a reaction medium. For example, utilization of kerosine or paraffinic hydrocarbons as the reaction medium has been disclosed in U.S. Pat. No. 2,111,973 and British Patent 181,673, as well as by Yura and Matsui in Journal of Industrial Chemistry (Kogyo Kagaku Zasshi in Japanese, vol. 47, p. 817). As another example, the use of aliphatic, alicyclic hydrocarbons, aromatic hydrocarbons or aromatic ethers as the reaction medium has been disclosed in JP-B 2-35732 (also in U.S. Pat. No. 4,633,024 and European Patent 92,772 as declaration of priority with regard to the Japanese patent; the U.S. Patent discloses only a limited examples of aromatic hydrocarbons).

Even in the case of these prior art processes in which inert solvents are used as the reaction medium, an alkali salt of aromatic sulfonic acid and an alkali metal hydroxide to be used as the starting materials cannot be dispersed to a satisfactory level in some of these reaction media, or do not disperse at all in some cases, thus resulting in the separation of these starting materials and the reaction medium from one another and subsequently in the adhesion of the separated compounds to the wall and impeller blades in a reactor vessel. For example, even when the inert solvents disclosed in the aforementioned U.S. Pat. No. 2,111,973 and JP-B 2-35732 (also in U.S. Pat. No. 4,633,024 and European Patent 92,772 as declaration of priority with regard to the Japanese patent) are used, high yield production of an aromatic hydroxy compound cannot be attained because of insufficient reaction due to phase separation of the reaction mixture. In addition to these problems, because of markedly different temperature levels between the reactor wall and the contents in the reactor owing to insufficient dispersion, it is difficult to control the reaction temperature within an optimum range and the unstable temperature control results in tar formation. Also, because of these problems, a reaction mixture cannot be discharged smoothly from a reactor vessel and therefore a continuous reaction system cannot be accomplished.

For the purpose of overcoming these problems involved in the prior art, the inventors of the present invention have conducted intensive studies on the reaction of an aromatic sulfonic acid alkali metal salt and/or an aromatic sulfonic acid with an alkali metal hydroxide in various reaction media and found that interfacial tension between a reaction medium and a melted product of alkali metal hydroxide was taking part in the phenomena which reveals the dispersion of the reaction mixture or non-dispersion of the reaction mixture being adhered to the wall of the reactor vessel. Since then, the present inventors have examined various techniques to reduce such an interfacial tension and found that the alkali fusion reaction can be effected in completely uniform dispersion phase by the use of a small amount of a surface active agent even in the case of the use of a reaction medium which usually causes adhesion of reaction materials to the wall and impeller blades in a reactor and subsequently impedes operations of the reaction. The present invention has been accomplished as a result of these efforts. An alkali fusion reaction is carried out at a high temperature under strong alkaline conditions. Astonishingly, the present inventors have found that even in such a hard reaction conditions a wide variety of surface active agents is effective in the process of this invention.

SUMMARY OF THE INVENTION

In view of the above, it therefore becomes an object of the present invention to provide an industrially useful process for the production of an aromatic hydroxy compound which comprises reacting an aromatic sulfonic acid alkali metal-salt and/or an aromatic sulfonic acid with an alkali metal hydroxide wherein the reaction is effected by uniformly dispersing these materials in a reaction medium. By employing this process, the product can be obtained with high purity, high yield and high selectivity using a minimum amount of the alkali metal hydroxide.

Particularly, according to the present invention, there is provided a process for the production of an aromatic hydroxy compound which comprises reacting an aromatic sulfonic acid alkali metal salt and/or an aromatic sulfonic acid with an alkali metal hydroxide in a reaction medium comprising at least one compound selected from the group consisting of aliphatic hydrocarbons, alicyclic hydrocarbons and aromatic hydrocarbons in the presence of a surface active agent not including cationic surface active agent. Preferably, the aromatic sulfonic acid alkali metal salt is selected from 2,6-naphthalenedisulfonic acid alkali metal salts, 2-naphthol-6-sulfonic acid alkali metal salts, 2-naphthalenesulfonic acid alkali metal salts, quinoline-8-sulfonic acid alkali metal salts and 4,4'-biphenyldisulfonic acid alkali metal salts, and the aromatic sulfonic acid is selected from 2, 6-naphthalenedisulfonic acid, 2 -naphthol-6-sulfonic acid, 2-naphthalenesulfonic acid, quinoline-8-sulfonic acid and 4,4'-biphenyldisulfonic acid.

Other objects and advantages will be made apparent as the description progresses.

DETAILED DESCRIPTION OF THE INVENTION

The aromatic sulfonic acid alkali metal salt to be used as one of the starting materials in the process of the present invention consists of an aromatic sulfonic acid and an alkali metal. Such an aromatic sulfonic acid is an aromatic compound having at least one sulfonic acid group in its structure, which is selected from monocyclic aromatic hydrocarbons, polycyclic aromatic hydrocarbons, condensed polycyclic aromatic hydrocarbons and hydrocarbons having a condensed ring consisting of an aromatic ring and a heterocyclic ring, as well as partially hydrogenated products thereof, each of these hydrocarbons having at least one sulfonic acid group in its molecule. Illustrative examples of such aromatic sulfonic acids include benzene, naphthalene, anthracene, phenanthrene, biphenyl, terphenyl, diphenyl alkane, triphenyl alkane, pyridine, quinoline, tetraline and the like. Useful alkali metals include for example sodium, potassium, lithium and the like. Aromatic sulfonic acids to be used together with or instead of the aromatic sulfonic acid alkali metal salts are the same as those described above. In addition to the sulfonic acid group, the aromatic sulfonic acid alkali metal salts or the aromatic sulfonic acids may contain other substitutional groups which do not contribute to the reaction, such as alkyl benzene, alkyl naphthalene, alkyl biphenyl, phenol, naphthol, hydroxybiphenyl, benzoic acid, phthalic acid, naphthoic acid, anthraquinone, naphthylamine and the like.

Illustrative examples of the aromatic sulfonic acid alkali metal salts include 2,6-naphthalenedisulfonic acid alkali metal salts, 2-naphthol-6-sulfonic acid alkali metal salts, 2-naphthalenesulfonic acid alkali metal salts, quinoline-8-sulfonic acid alkali metal salts, 4,4'-biphenyldisulfonic acid alkali metal salts and the like, with the counterpart alkali metals being sodium, potassium and the like. Illustrative examples of the aromatic sulfonic acids include 2,6-naphthalenedisulfonic acid, 2-naphthol-6-sulfonic acid, 2-naphthalenesulfonic acid, quinoline-8-sulfonic acid, 4,4'-biphenyldisulfonic acid and the like.

According to the present invention, each illustrative compound of the aromatic sulfonic acid alkali metal salt and/or the aromatic sulfonic acid as the starting material is selected in accordance with the aromatic hydroxy compound to be produced. For example, by the use of the process of the present invention, 2,6-dihydroxynaphthalene is produced from 2,6-naphthalenedisulfonic acid or 2-naphthol-6-sulfonic acid or an alkali metal salt thereof, 2- naphthol is produced from 2-naphthalenesulfonic acid or an alkali metal salt thereof, 8-hydroxyquinoline from quinoline-8-sulfonic acid or an alkali metal salt thereof, and 4,4'-dihydroxybiphenyl from 4,4'-biphenyldisulfonic acid or an alkali metal salt thereof, each product showing improved yield, selectivity and hue (or less coloration).

With regard to an alkali metal hydroxide as the other starting material to be used in the process of the present invention, sodium hydroxide or potassium hydroxide may be used preferably. The alkali metal hydroxide may be used in such an amount that a mixing ratio of the starting materials becomes 2 to 10 alkali metal hydroxide molecules, preferably 2 to 7 molecules, per one sulfonic acid group contained in an aromatic sulfonic acid alkali metal salt and/or an aromatic sulfonic acid to be used. For example, when an aromatic sulfonic acid alkali metal salt having one sulfonic acid group in its molecule is used, 2 to 10 moles, preferably 2 to 7 moles, of an alkali metal hydroxide may be used per one mole of the aromatic sulfonic acid alkali metal salt. The alkali metal hydroxide may be used in various forms such as flake, aqueous solution and the like.

According to the process .of the present invention, most preferred combination of the aromatic sulfonic acid alkali metal salt with the alkali metal hydroxide is: sodium 2, 6-naphthalenedisulfonate, potassium 2,6-naphthalenedisulfonate, sodium 2-naphthol-6-sulfonate or potassium 2-naphthol-6-sulfonate with potassium hydroxide; sodium 2-naphthalenesulfonate with sodium hydroxide; sodium quinoline-8-sulfonate with sodium hydroxide; and sodium 4,4'-biphenyldisulfonate or potassium 4,4'-biphenyldisulfonate with potassium hydroxide. Most preferred combination of the aromatic sulfonic acid with the alkali metal hydroxide is: 2,6-naphthalenedisulfonic acid or 2-naphthol-6-sulfonic acid with potassium hydroxide; 2-naphthalenesulfonic acid with sodium hydroxide; quinoline-8-sulfonic acid with sodium hydroxide; and 4,4'-biphenyldisulfonic acid with potassium hydroxide.

According to the process of the present invention, the aromatic sulfonic acid alkali metal salt and/or the aromatic sulfonic acid is reacted with the alkali metalhydroxide in a reaction medium in the presence of a surface active agent.

The reaction medium to be used is at least one compound having a boiling point of higher than the reaction temperature, which is selected from the group consisting of aliphatic hydrocarbons, alicyclic hydrocarbons and aromatic hydrocarbons. Illustrative examples of such aliphatic and alicyclic hydrocarbons include paraffin, liquid paraffin (white oil), kerosine, light oil and the like. Illustrative examples of aromatic hydrocarbons include: alkylbenzenes; alkylnaphthalenes; diaryls such as ethylbiphenyl, diethylbiphenyl, triethylbiphenyl and the like; complete or partial hydrogenation products of diaryls; triaryls such as terphenyls and the like; complete or partial hydrogenation products of triaryls such as hydrogenated terphenyl and the like; diaryl alkanes such as 1-phenyl-l-(2,3-dimethyl phenyl)-ethane, benzyltoluene and the like; complete or partial hydrogenation products of diaryl alkanes; triaryl alkanes such as dibenzyltoluene and the like; complete or partial hydrogenation products of triaryl alkanes; and styrene oligomers or complete or partial hydrogene products of styrene oligomers.

These reaction media, or inert media, may be used alone or as a mixture of two or more in an amount of from 0.1 to 50 weight parts, preferably from 1 to 10 weight parts, based on one weight part of a mixture of the aromatic sulfonic acid alkali metal salt and/or the aromatic sulfonic acid and the alkali metal hydroxide.

Anionic surface active agents, nonionic surface active agents and/or amphoteric surface active agents may be used in the present invention.

Illustrative examples of the surface active agents to be used in the present invention are as follows. The anionic surface active agents having carboxyl group include: saturated fatty acid salts such as sodium stearates and the like, and unsaturated fatty acid salts such as sodium oleates and the like.

The anionic surface active agents having sulfonic acid group include: alkylbenzene sulfonates such as sodium dodecylbenzene sulfonates and the like, alkane sulfonates, and alkene sulfonates such as sodium tetradecene sulfonates and the like.

The anionic surface active agents having sulfate linkage include salts of alkyl sulfate such as sodium lauryl sulfate.

The anionic surface active agents having sulfonic acid group and carboxyl group or ester linkage include salts of alkyl sulfosuccinic acid such as sodium dioctyl sulfosuccinate and the like, and salts of sulfo fatty acid ester.

The anionic surface active agents having sulfate linkage, hydroxyl group and carboxyl group or ester linkage include salts of sulfated monoglyceride of fatty acid such as sodium lauric acid monoglyceride sulfate.

The anionic surface active agents having a polyoxyalkylene chain and sulfate linkage include salts of polyoxyalkylene alkylether sulfate such as sodium polyoxyethylene laurylether sulfate and the-like, and salts of polyoxyalkylene alkylphenylether sulfate such as sodium polyoxyethylene nonylphenylether sulfate and the like.

The anionic surface active agents having a polyoxyalkylene chain and sulfonic acid group include salts of polyoxyalkylene alkylphenylether sulfonate such as sodium polyoxyethylene nonylphenylether surfonate and the like.

The anionic surface active agents having sulfonic acid group and amide group include salts of methyl taurine such as sodium stearoyl methyl tauride and the like.

The phosphoric acid based anionic surface active agents include salts of polyoxyalkylene alkylether phosphoric acid ester such as sodium polyoxyethylene laurylether phosphate and the like.

The ether type nonionic surface active agents having a polyoxyalkylene chain include polyoxyalkylene alkylethers such as polyoxyethylene lauryl ether and the like, and polyoxyalkylene alkylphenyl ethers such as polyoxyethylene nonylphenyl ether and the like.

The nonionic surface active agents having hydroxyl group and ester linkage include fatty acid monoglycerides such as stearic acid monoglyceride and the like, sorbitan fatty acid esters such as sorbitan monolaurate and the like, polyoxyethylene sorbitan fatty acid esters such as polyoxyethylene sorbitan monolaurate and the like, and sucrose fatty acid esters such as sucrose monolaurate and the like.

The nonionic surface acitive agents having amide linkage and hydroxyl group include alkyl alkanol amides such as lauric acid diethanolamide and the like.

The nonionic surface active agents having amino group and a polyoxyalkylene chain include polyoxyalkyleneamines such as polyoxyethylene coconut-alkyamine and the like.

The nonionic surface acitve agents having amide linkage and a polyoxyalkylene chain include polyoxyalkyleneamides such as polyoxyethylene oleic acid amide and the like.

The nonionic surface active agents having amine oxide group include alkylamineoxides such as dodecyldimethyl amine oxide and the like.

The amphoteric surface active agents having amino group and carboxyl group include alkyl betaines such as dimethyl coconut-alkyl betaine and the like, alkyl imidazolium betaines such as 2-alkyl-N-carboxyethyl-N-hydroxyethyl imidazolium betaine and the like, and amino aicds.

Additionally, fluoride surface active agents in which at least partly hydrogen atoms in the alkyl groups are substituted with fluorine atoms such as salts of perfluorooctanoic acid and polysiloxanes (silicone based surface active agents) are also useful.

The polymer surface active agents having a lower value of surface tension are also useful.

The alkali fusion reaction conditions of this invention are conducted at a temperature of 250° C. to 350° C. under strong alkaline conditions. Even in such hard conditions the above mentioned surface active agents are effective in the present process. However, cationic surface active agents do not reveal any effects in the present process.

These surface active agents may be used alone or as a mixture of two or more in an amount of from 0.01 by weight or more, preferably from 0.01 to 1% by weight, based-on the alkali metal hydroxide to be used.

Since the reaction process is not strictly limited, various techniques may be employed such as: a process in which a mixture consisting of the aromatic sulfonic acid alkali metal salt and/or the aromatic sulfonic acid, the alkali metal hydroxide, the reaction medium and the surface active agent i s firstly prepared, temperature of the mixture is increased to a predetermined level and then the reaction is carried out with agitation; a process in which the alkali metal hydroxide, the reaction medium and the surface active agent are mixed in advance with agitation, the aromatic sulfonic acid alkali metal salt and/or the aromatic sulfonic acid are added to the mixture and .then the reaction is effected by increasing the temperature to a predetermined level; and a process in which the aromatic sulfonic acid alkali metal salt and/or the aromatic sulfonic acid are mixed with the reaction medium in advance with agitation, temperature is increased to a certain level, the surface active agent and the alkali metal hydroxide are added to the mixture and then the react ion i s effected by increasing the temperature to a predetermined reaction temperature level.

The reaction temperature suitable for the process of the present invention may vary depending on the kind of the aromatic sulfonic acid alkali metal salt and/or the aromatic sulfonic acid to be used as the starting material, but may generally be in the range of from 250° to 350° C. Preferably, the reaction temperature may be 310° to 350° C. to obtain 2,6-dihydroxynaphthalene, 280° to 350° C. to obtain β-naphthol, 260° to 330° C. to obtain 8-hydroxyquinoline, 280° to 350° C. to obtian 4,4'-dihydroxybiphenyl. The reaction may be carried out for a period of from 0.1 to 10 hours, preferably in an inert gas atmosphere such as nitrogen, by either a batch or continuous means.

After completion of the reaction, an aqueous solution containing an alkali metal salt of an aromatic hydroxy compound thus formed by the reaction and the alkali metal hydroxide remained after the reaction is obtained by either diluting the resulting reaction mixture directly with water and then separating the reaction medium or by firstly separating the reaction product from the reaction medium by means of filtration or the like and then diluting the thus separated product-containing portion with water. Thereafter, by-products of the reaction such as sulfites and the like are separated from the thus obtained aqueous solution, which is then subjected to neutralization with an acid.

As an acid for use in the neutralization step, a mineral acid such as sulfuric acid, hydrochloric acid or the like or acid sodium sulfite, sulfur dioxide, carbon dioxide or the like may be used.

After the neutralization step, the resulting reaction mixture may be subjected to filtration or solvent extraction to isolate the aromatic hydroxy compound of interest. In this instance, if necessary, the product may be purified by means of distillation, sublimation, recrystallization and the like.

Recrystallization may be preferred to obtain 2,6-dihydroxynaphthalene or 4,4'-dihydroxybiphenyl, distillation may be preferred to obtain 2-naphthol or 8-hydroxyquinoline.

In these processes, impurities derived from surface active agents, if they are remain, can be removed.

The aromatic hydroxy compounds obtained by the process of the present invention can be used in many applications such as: 2,6-dihydroxynaphthalene and 4,4'-dihydroxybiphenyl for use in resin monomers and the like; 2-naphthol for use in various intermediate compounds; and 8-hydroxyquinoline for use in agricultural chemicals and the like.

EXAMPLES

The following inventive and comparative examples are provided to further illustrate the present invention.

Example 1

A reaction vessel was charged with 364 g of potassium 2,6-naphthalenedisulfonate, 651 g of 86% potassium hydroxide, 3.3 g of sodium oleate and, as a reaction medium, 2500 g of a hydrogenated terphenyl mixture. After mixing these materials and replacing the atmosphere in the reaction vessel with nitrogen gas, temperature of the mixture was increased until potassium hydroxide melted and then dehydration was carried out by gradually increasing the temperature to 330° C. with stirring. Thereafter, the reaction was carried out at 330° C. for 3 hours with stirring. During the reaction step, temperature difference between the bottom and upper parts in the vessel was hardly observed. When conditions inside the vessel were observed after cooling the reaction system, granular solid materials were dispersed in the reaction medium and no adhered materials were found on the vessel wall. The reaction mixture thus obtained was mixed with 2 liters of water to separate organic (hydrogenated terphenyl) phase. Thereafter, the main product of the reaction was recovered from the resulting aqueous solution by precipitating the products with dilute sulfuric acid and subsequently extracting it with methyl isobutyl ketone. Liquid chromatographic analysis of the main product thus isolated revealed that 139.5 g of 2,6-dihydroxynaphthalene was formed by the reaction with a conversion ratio of 99% and a selectivity of 88%. The results are shown in Table 1.

The same dispersion effect was revealed by using other salts of fatty acid.

Comparative Example 1

A reaction vessel was charged with 364 g of potassium 2,6-naphthalenedisulfonate and 560 g of 50% potassium hydroxide and then, after mixing, with 2500 g of a hydrogenated terphenyl mixture. After replacing the atmosphere in the reaction vessel with nitrogen gas, temperature of the mixture was gradually increased to 310° C. with stirring to allow dehydration. Thereafter, the reaction was carried out at 310° C. for 3 hours with stirring. In this instance, adhered materials were found on the wall and impeller blades in the reaction vessel during the temperature-increasing step, and temperature difference between the bottom and upper parts in the vessel reached about 50° C. When conditions inside the vessel were observed after cooling the reaction system, no dispersion of the materials was found while a large quantity of adhered materials were found on the vessel wall and impeller blades. The reaction mixture thus obtained was mixed with 2 liters of water to separate organic (hydrogenated terphenyl) phase. Thereafter, the main product of the reaction was recovered from the resulting aqueous solution by precipitating the product with dilute sulfuric acid and subsequently extracting it with methyl isobutyl ketone. Liquid chromatographic analysis of the main product thus isolated revealed that 42.7 g of 2,6-dihydroxynaphthalene was formed by the reaction with a conversion ratio of 46% and a selectivity of 58%. In addition, the thus isolated 2,6-dihydroxynaphthalene was markedly colored. The results are shown in Table 1.

Comparative Example 2

The reaction of Example 1 was repeated except that sodium oleate was not used. In this instance, adhered materials were found on the wall and impeller blades in the reaction vessel during the temperature-increasing step, and temperature difference between the bottom and upper parts in the vessel reached about 50° C. When conditions inside the vessel were observed after cooling the reaction system, no dispersion of the materials was found while a large quantity of adhered materials were found on the vessel wall and impeller blades. The reaction mixture thus obtained was mixed with 2 liters of water to separate organic (hydrogenated terphenyl) phase. Thereafter, the main product of the reaction was recovered from the resulting aqueous solution by precipitating the product with dilute sulfuric acid and subsequently extracting it with methyl isobutyl ketone. Liquid chromatographic analysis of the main product thus isolated revealed that 111.1 g of 2,6-dihydroxynaphthalene was formed by the reaction with a conversion ratio of 99% and a selectivity of 70%. In addition, the thus isolated 2,6-dihydroxynaphthalene was markedly colored. The results are shown in Table 1.

Example 2

A reaction vessel was charged with 246 g of sodium 2-naphthol-6-sulfonate, 390.7 g of 86% potassium hydroxide, 2.0 g of sodium tetradecenesulfonate and, as a reaction medium, 1200 g of a mineral oil (a mixture of aliphatic hydrocarbons and alicyclic hydrocarbons). After mixing these materials and replacing the atmosphere in the reaction vessel with nitrogen gas, temperature of the mixture was increased until potassium hydroxide melted and then dehydration was carried out by gradually increasing the temperature to 330° C. with stirring. Thereafter, the reaction was carried out at 330° C. for 3.5 hours with stirring. During the reaction step, temperature difference between the bottom and upper parts in the vessel was hardly observed. When conditions inside the vessel were observed after cooling the reaction system, granular solid materials were dispersed in the reaction medium and no adhered materials were found on the vessel wall. The reaction mixture thus obtained was mixed with 2 liters of water to separate organic (mineral oil) phase. Thereafter, the main product of the reaction was recovered from the resulting aqueous solution by precipitating the product with dilute sulfuric acid and subsequently extracting it with methyl isobutyl ketone. Liquid chromatographic analysis of the main product thus isolated revealed that 138.0 g of 2,6-dihydroxynaphthalene was formed by the reaction with a conversion ratio of 99% and a selectivity of 87%. The results are shown in Table 1.

Comparative Example 3

The process of Example 2 was repeated except that sodium tetradecenesulfonate was not used. 2,6-dihydroxynaphthalene was formed by the reaction with a convension ratio of 99% and a selectivity of 71%. The results are shown in Table 1.

TABLE 1

| | Starting material*[1] (g) | Medium (g) | Surface active agent (g) | KOH molar ratio | Temp (°C.) | Time (hr) | Dispersion | Conversion ratio (%) | Selectibity (%) |
|---|---|---|---|---|---|---|---|---|---|
| Example 1 | 2,6-NDSK*[2] (364) | hydrogenated terphenyl mixture (2500) | sodium oleate (3.3) | 10 | 330 | 3 | good | 99 | 88 |
| Comparative Example 1 | 2,6-NDSK (364) | hydrogenated terphenyl mixture (2500) | not added | 5 | 310 | 3 | not dispersed | 46 | 58 |
| Comparative Example 2 | 2,6-NDSK (364) | hydrogenated terphenyl mixture (2500) | not added | 10 | 330 | 3 | not dispersed | 99 | 70 |
| Example 2 | 2N6SNa*[3] (246) | mineral oil (1200) | sodium tetradecene-sulfonate (2.0) | 6 | 330 | 3.5 | good | 99 | 87 |
| Comparative Example 3 | 2N6SNa (246) | mineral oil (1200) | not added | 6 | 330 | 3.5 | not dispersed | 99 | 71 |

*[1]: Starting material; aromatic sulfonic acid alkali metal salt or aromatic sulfonic acid
*[2]: 2,6-NDSK; potassium 2,6-naphthalenedisulfonate
*[3]: 2N6SNa; sodium 2-naphthol-6-sulfonate

Examples 3–18 and Comparative Example 4

The process of Example 2 was repeated except that other kinds of surface active agents as shown in Table 2 were used respectively. The amount of the surface active agent was 0.5 % by weight as an effective component based-on the potasium hydroxide. Results of identification of the product and measurement of its conversion ratio and seecctivity are shown in Table 2.

TABLE 2

| | Classification of surface active agent | Surface active agent | Dispersion | Conversion ratio (%) | Selectivity (%) |
|---|---|---|---|---|---|
| Example 3 | anionic | sodium oleate | good | 99 | 86 |
| Example 4 | anionic | sodium stearate | good | 99 | 83 |
| Example 5 | anionic | sodium n-dodecylbenzenesulfonate | good | 99 | 86 |
| Example 6 | anionic | sodium laurylsulfonate | good | 99 | 85 |
| Example 7 | anionic | sodium polyoxyethylene nonylphenyl ether sulfate | good | 99 | 85 |
| Example 8 | anionic | sodium polyoxyethylene lauryl ether sulfate | good | 99 | 86 |
| Example 9 | anionic | sodium perfluorooctanoate | good | 99 | 86 |
| Example 10 | anionic | sodium polyoxyethylene lauryl ether phosphate | good | 99 | 84 |
| Example 11 | anionic | sodium dioctyl sulfosuccinate | good | 99 | 80 |
| Example 12 | nonionic | sorbitan-monolaurate | good | 99 | 85 |
| Example 13 | nonionic | polyoxyethylene sorbitan monolaurate | good | 99 | 84 |
| Example 14 | nonionic | polyoxyethylene nonyl phenyl ether-ethylen oxide (10 moles) additives | good | 99 | 86 |
| Example 15 | nonionic | dodecyldimethylamineoxide | good | 99 | 80 |
| Example 16 | nonionic | lauryl diethanolamide | good | 99 | 84 |
| Example 17 | amphoteric | dimethylcoconut alkyl betaine | good | 99 | 85 |
| Example 18 | amphoteric | 2-alkyl-N-carboxyethyl-N-hydroxyethyl imidazolium betaine | good | 99 | 85 |
| Comparative | cationic | lauryl trimethyl ammonium chloride | not dispersed | 99 | 69 |

TABLE 2-continued

| Classification of surface active agent | Surface active agent | Dispersion | Conversion ratio (%) | Selectivity (%) |
|---|---|---|---|---|
| Example 4 | | | | |

Example 19

A reaction vessel was charged with 230 g of sodium 2-naphthalenesulfonate, 230 g of 50% sodium hydroxide, 0.6 g of sodium oleate and 1440 g of a mineral oil (a mixture of aliphatic hydrocarbons and alicyclic hydrocarbons). After mixing these materials and replacing the atmosphere in the reaction vessel with nitrogen gas, temperature of the mixture was gradually increased to 310° C. with stirring to allow hydration. Thereafter, the reaction was carried out at 310° C. for 3 hours with stirring. During the reaction step, temperature difference between the bottom and upper parts in the vessel was hardly observed. When conditions inside the vessel were observed after cooling the reaction system, granular solid materials were dispersed in the reaction medium and no adhered materials were found on the vessel wall. The reaction mixture thus obtained was mixed with 2 liters of water to separate organic phase. Thereafter, the main product of the reaction was recovered from the resulting aqueous solution by precipitating the product with dilute sulfuric acid and subsequently extracting it with methyl isobutyl ketone. Liquid chromatographic analysis of the main product thus isolated revealed that 136.0 g of 2-naphthol was formed by the reaction with a recovery yield of 94.3%.

The same dispersion effect was revealed by using sodium tetradecenesulfonate or polyoxyethylene nonylphenyletherethylene oxide (10 moles) adduct.

Comparative Example 5

The reaction of Example 19 was repeated except that sodium oleate was not used. In this instance, adhered materials were found on the wall and impeller blades in the reaction vessel during the temperature-increasing step, and temperature difference between the bottom and upper parts in the vessel reached about 50° C. When conditions inside the vessel were observed-after cooling the reaction system, no dispersion of the materials was found while a large quantity of adhered materials were found on the vessel wall and impeller blades. The reaction mixture thus obtained was mixed with 2 liters of water to separate organic (mineral oil) phase. Thereafter, the main product of the reaction was recovered from the resulting aqueous solution by precipitating the product with dilute sulfuric acid and subsequently extracting it with methyl isobutyl ketone. Liquid chromatographic analysis of the main product thus isolated revealed that 93.7 g of 2-naphthol was formed by the reaction with a recovery yield of 65%.

Example 20

A reaction vessel was charged with 390.5 g of potassium 4,4'-biphenyldisulfonate, 897 g of 50% potassium hydroxide, 4.5 g of sodium tetradecene sulfonate and 3366 g of a mineral oil (a mixture of aliphatic hydrocarbons and alicyclic hydrocarbons). After mixing these materials and replacing the atmosphere in the reaction vessel with nitrogen gas, temperature of the mixture was gradually increased to 310° C. with stirring to allow hydration. Thereafter, the reaction was carried out at 310° C. for 3 hours with stirring. During the reaction step, temperature difference between the bottom and upper parts in the vessel was hardly observed. When conditions inside the vessel were observed after cooling the reaction system, granular solid materials were dispersed in the reaction medium and no adhered materials were found on the vessel wall. The reaction mixture thus obtained was mixed with 2 liters of water to separate organic phase. Thereafter, the main product of the reaction was recovered from the resulting aqueous solution by precipitating the product with dilute sulfuric acid and subsequently extracting it with methyl isobutyl ketone. Liquid chromatographic analysis of the main product thus isolated revealed that 175.0 g of 4,4'-dihydroxybiphenyl was formed by the reaction with a recovery yield of 94%.

The same dispersion effect was revealed by using sodium oleate or polyoxyethylene nonylphenyletherethylene oxide (10 moles) adduct.

Comparative Example 6

The reaction of Example 20 was repeated except that sodium tetradecene sulfonate was not used. In this instance, adhered materials were found on the wall and impeller blades in the reaction vessel during the temperature-increasing step, and temperature difference between the bottom and upper parts in the vessel reached about 50° C. When conditions inside the vessel were observed after cooling the reaction system, no dispersion of the materials was found while a large quantity of adhered materials were found on the vessel wall and impeller blades. The reaction mixture thus obtained was mixed with 2 liters of water to separate organic (mineral oil) phase. Thereafter, the main product of the reaction was recovered from the resulting aqueous solution by precipitating the product with dilute sulfuric acid and subsequently extracting it with methyl isobutyl ketone. Liquid chromatographic analysis of the main product thus isolated revealed that 135.9g of 4,4'-dihydroxybiphenyl was formed by the reaction with a recovery yield of 73%.

Example 21

A reaction vessel was charged with 209 g of quinoline-8-sulfonic acid, 159 g of sodium hydroxide, 2.5 g of sodium tetradecene sulfonate and, as a reaction medium, 208 g of a mineral oil (a mixture of aliphatic hydrocarbons and alicyclic hydrocarbons). After mixing these materials and replacing the atmosphere in the reaction vessel with nitrogen gas, temperature of the mixture was gradually increased to 305° C. with stirring and then immediately cooled. When conditions inside the vessel were observed after cooling the reaction system, granular solid materials were dispersed in the reaction medium and no adhered materials were found on the vessel wall. The reaction mixture thus obtained was mixed with 3 liters of water to separate organic phase. Thereafter, the main product of the reaction was recovered from the resulting aqueous solution by precipitating the product with dilute sulfuric acid and subsequently extracting it with chloroform. Liquid chromatographic analysis of the main product thus isolated revealed that 135.4 g of 8-hydroxyquinoline was formed by the reaction with a conversion ratio of 97% and a selectivity of 96%.

The same dispersion effect was revealed by using sodium oleate or polyoxyethylene nonylphenylether-ethylene oxide (10 moles) adduct.

Thus, it is apparent that there has been provided, in accordance with the present invention, a process for the production of an aromatic hydroxy compound from an aromatic sulfonic acid alkali metal salt and/or an aromatic sulfonic acid. Since the reaction process of the present invention can be carried out in a completely dispersed phase of the materials and within a uniformly distributed range of temperature of the reaction mixture, the reaction temperature can be controlled easily and the aromatic hydroxy compound can be produced with high purity, high yield and high selectivity. Also, since the amount of the alkali metal hydroxide can be reduced, discharge and transportation of the reaction product can be performed easily, thus rendering possible continuous operation of the reaction and therefore showing a high practical application value of the process of the present invention to industrial scale operation. In addition, since easily available solvents such as mineral oil can be used in the reaction system, the process of the present invention is suitable for industrial scale production of aromatic hydroxy compounds.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A process for producing an aromatic hydroxy compound comprising the step of reacting
    (A) an alkali metal salt of an aromatic sulfonic acid and/or an aromatic sulfonic acid and
    (B) an alkali metal hydroxide, in a reaction medium
    (C) which comprises at least one compound selected from the group consisting of aliphatic hydrocarbons, alicyclic hydrocarbons and aromatic hydrocarbons, in the presence of
    (D) at least one additive compound selected from the group consisting of;
    fatty acid salts, aliphatic sulfonates, alkylaryl sulfonates other than the starting material, salts of alkyl sulfates, salts of alkyl sulfosuccinic acid ester, salts of sulfofatty acid ester,
    salts of sulfated monoglyceride of fatty acid,
    salts of polyoxyalkylene alkyl ether sulfate,
    salts of polyoxalkylene alkylphenylether sulfate,
    salts of polyoxyalkylene alkylphenylether sulfonate,
    salts of methyltaurine,
    salts of polyoxyalkylene alkylether phosphoric acid ester, polyoxyalkylene alkylethers, polyoxalkylene alkylphenyl ethers, fatty acid monoglycerides, polyoxyalkylene sorbitan fatty acid esters,
    sucrose fatty acid esters, alkyl alkanol amides, polyoxyalkyleneamines, polyoxyalkyleneamides, alkylaminoxides, and alkyl betaines wherein said additive compound (D) is used in an amount of from 0.01 to 1% by weight based on the alkali metal hydroxide (B).

2. The process for producing an aromatic hydroxy compound of claim 1 wherein said starting material (A) is selected from the group consisting of 2,6-naphthalenedisulfonic acid alkali metal salts, 2-naphthol-6-sulfonic acid alkali metal salts, 2,6-naphthalenedisulfonic acid and 2-naphthol-6-sulfonic acid.

3. The process for producing an aromatic hydroxy compound of claim 1 wherein said starting material (A) is selected from the group consisting of 2-naphthalenesulfonic acid alkali metal salts and 2-naphthalene sulfonic acid.

4. The process for producing an aromatic hydroxy compound of claim 1 wherein said starting material (A) is selected from the group consisting of quinoline-8-sulfonic acid alkali metal salts and quinoline-8-sulfonic acid.

5. The process for producing an aromatic hydroxy compound of claim 1 wherein said starting material (A) is 4,4'-biphenyldisulfonic acid.

* * * * *